(12) United States Patent
Wilson

(10) Patent No.: US 10,325,523 B2
(45) Date of Patent: Jun. 18, 2019

(54) LIGAMENT END-FEEL SIMULATOR

(71) Applicant: Steven Walter Wilson, Philadelphia, PA (US)

(72) Inventor: Steven Walter Wilson, Philadelphia, PA (US)

(73) Assignee: Steven W. Wilson, Philadelphia, PA (US)

( * ) Notice: Subject to any disclaimer, the term of this patent is extended or adjusted under 35 U.S.C. 154(b) by 508 days.

(21) Appl. No.: 15/055,639

(22) Filed: Feb. 29, 2016

(65) Prior Publication Data
US 2017/0249869 A1 Aug. 31, 2017

(51) Int. Cl.
*G09B 23/28* (2006.01)
*G09B 23/32* (2006.01)
*A61B 17/56* (2006.01)
*G09B 9/00* (2006.01)
*A61B 17/00* (2006.01)

(52) U.S. Cl.
CPC ............. *G09B 23/32* (2013.01); *A61B 17/56* (2013.01); *G09B 9/00* (2013.01); *A61B 2017/00716* (2013.01)

(58) Field of Classification Search
CPC .... G09B 23/28; G09B 23/285; G09B 23/286; G09B 23/30; G09B 23/32
USPC ......................................... 434/262, 267, 274
See application file for complete search history.

(56) References Cited

U.S. PATENT DOCUMENTS

| | | | | |
|---|---|---|---|---|
| 4,349,339 A | * | 9/1982 | Daniel ................... | G09B 23/32 434/274 |
| 4,850,877 A | * | 7/1989 | Mason ................. | A61B 5/1107 434/274 |
| 6,361,729 B1 | * | 3/2002 | Strover ................ | G09B 23/285 264/247 |
| 6,468,087 B2 | * | 10/2002 | Slocum .................. | G09B 23/32 434/262 |
| 7,699,615 B2 | * | 4/2010 | Sakezles ................ | G09B 23/28 434/274 |
| 7,748,984 B2 | * | 7/2010 | McAllister ............. | G09B 23/32 434/274 |
| 7,866,983 B2 | * | 1/2011 | Hemphill ............... | G09B 23/34 434/262 |
| 8,108,190 B2 | * | 1/2012 | Riener ................... | G09B 23/32 434/267 |
| 9,916,775 B2 | * | 3/2018 | McInnis ................. | G09B 23/32 |
| 2006/0051729 A1 | * | 3/2006 | Zeeff ...................... | G09B 23/32 434/274 |
| 2008/0286736 A1 | * | 11/2008 | Browne-Wilkinson ..................... | G09B 23/32 434/274 |
| 2014/0017650 A1 | * | 1/2014 | Romero ................ | G09B 23/30 434/270 |

* cited by examiner

*Primary Examiner* — Kurt Fernstrom

(57) ABSTRACT

The [Ligament End Feel Simulator] has the sole purpose of teaching athletic training students and other medical professionals what laxity of the anterior cruciate ligament feels like without the need for a live injured patient to be present. The novelty of the present invention comes from the non-existence of the present invention in the athletic training profession. Although a person not knowledgeable in the art can look at the present invention and recognize it as being a knee; the average person and even most medical professionals will not know that the device is meant to be used in conjunction with the Lachman manual special test.

6 Claims, 23 Drawing Sheets

Fig. 1.1

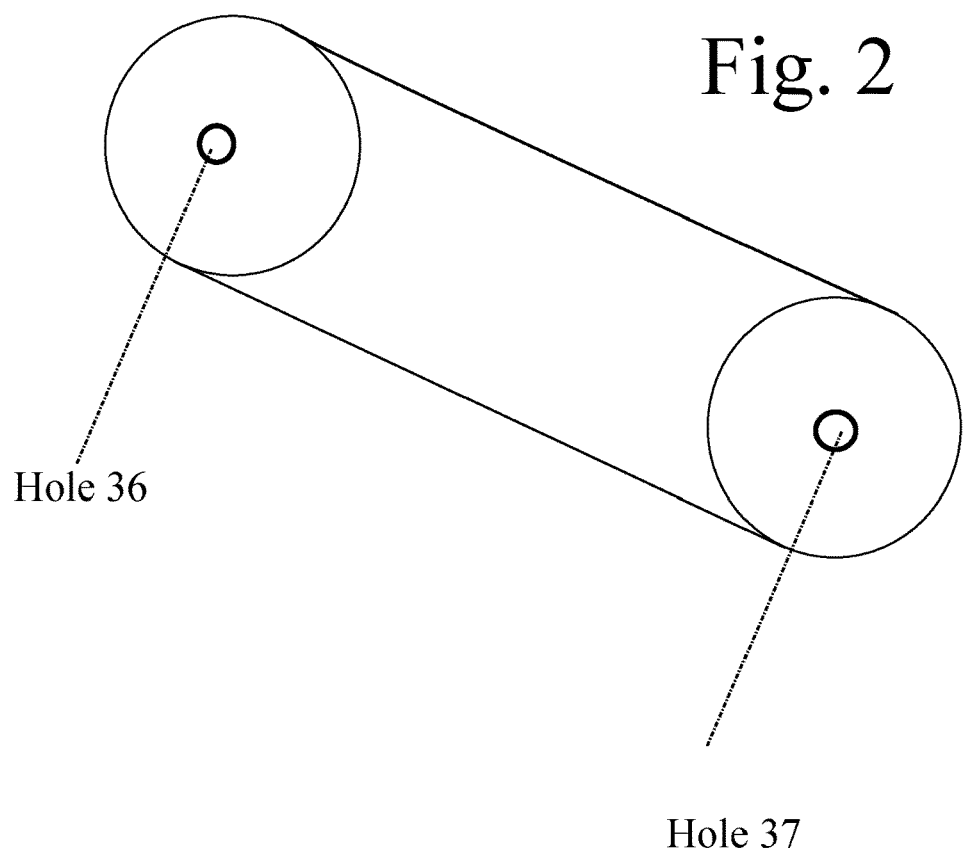
Fig. 2
Hole 36
Hole 37
Fig. 2.1

Fig. 4.2
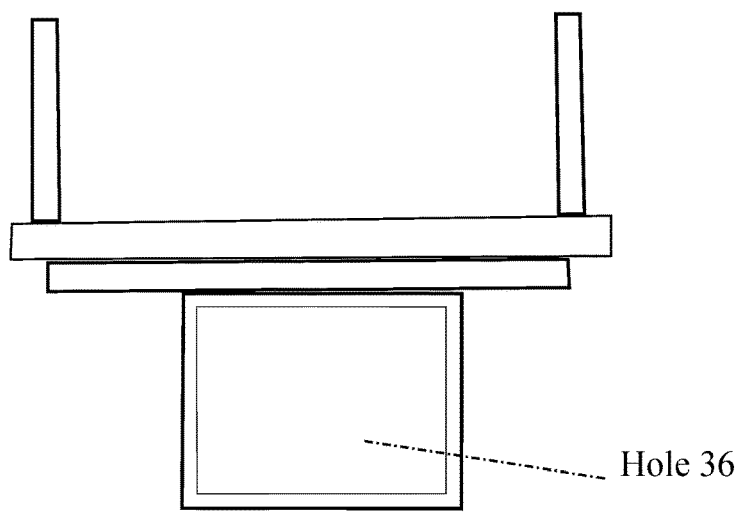
Fig. 4.3
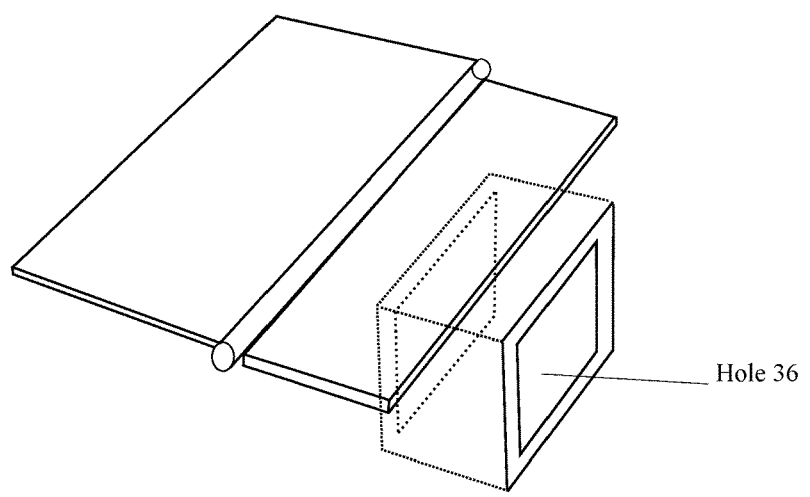

Fig. 5.1
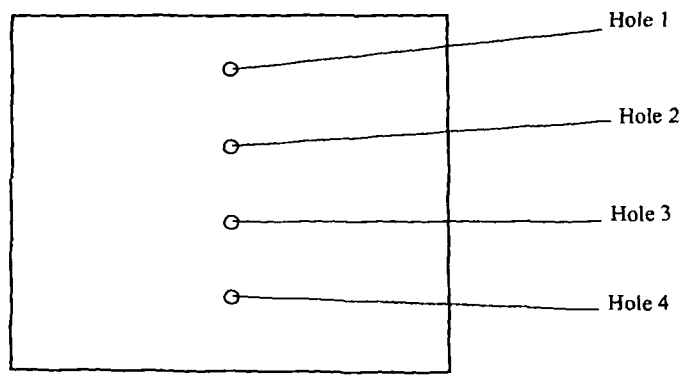
Fig. 5.2
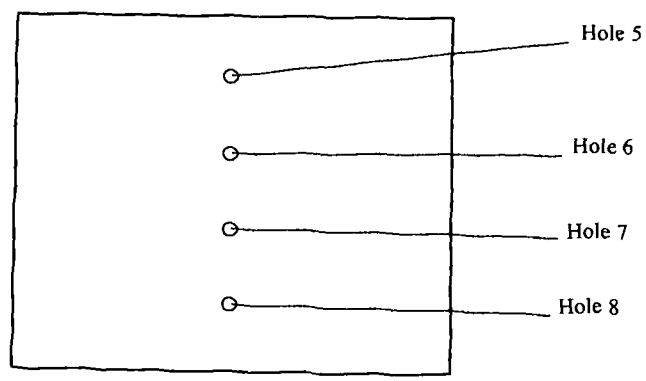

Fig. 5.3
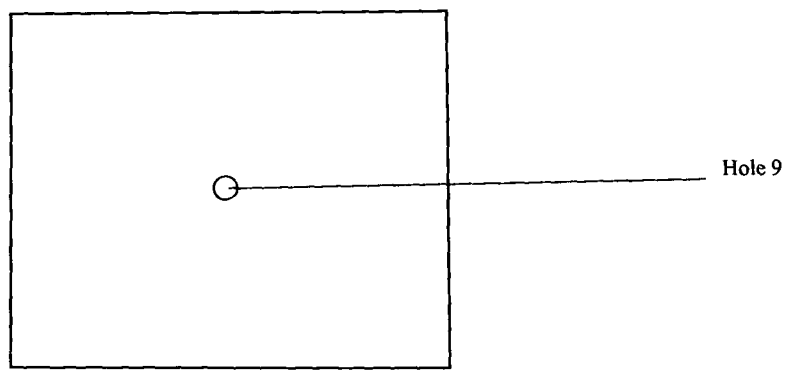

Fig 6.1
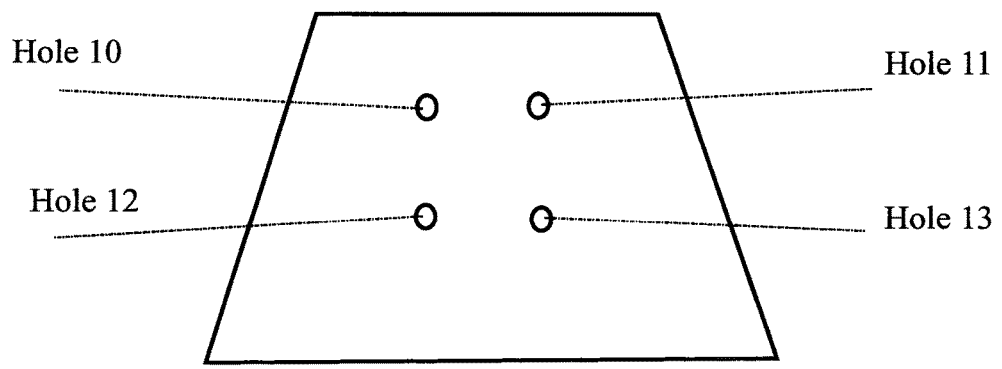
Fig. 6.2
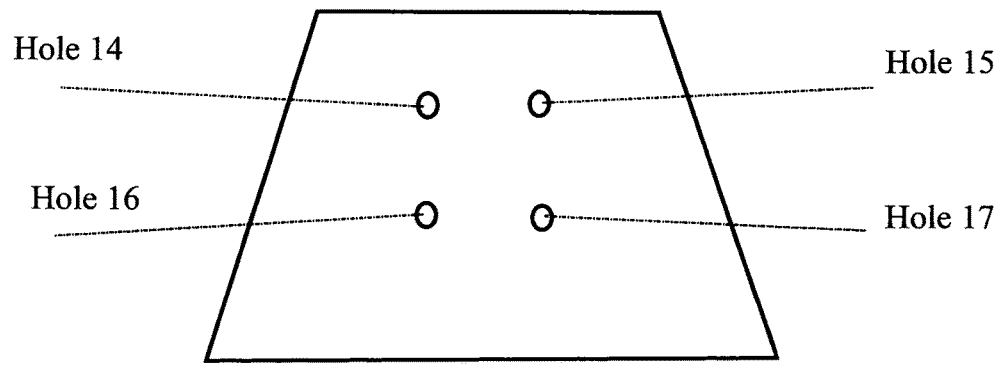

Fig. 6.3
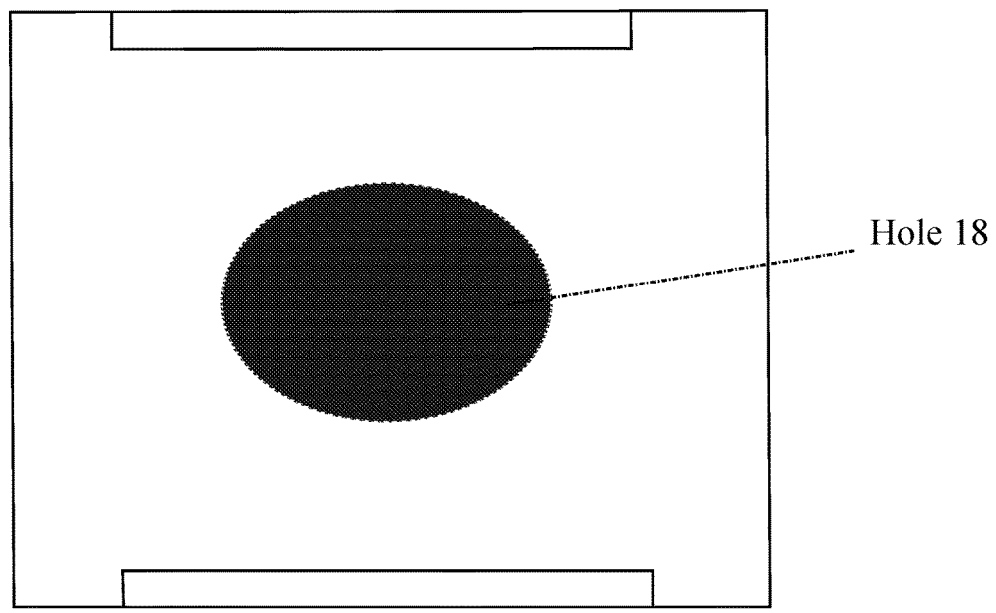

Fig. 6.4
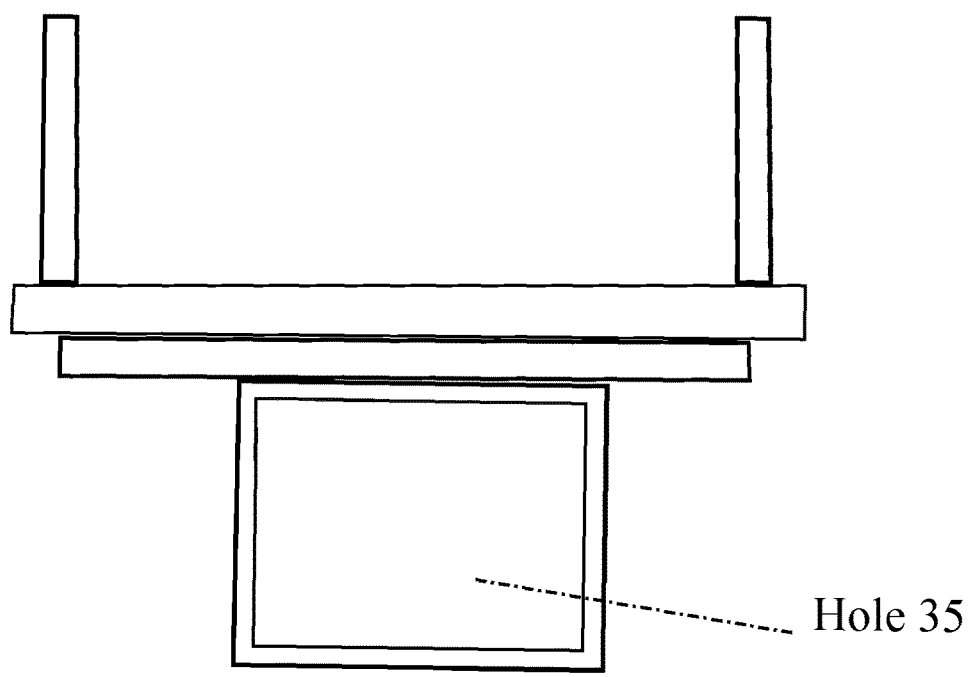

Fig. 7.1

Fig. 7.2
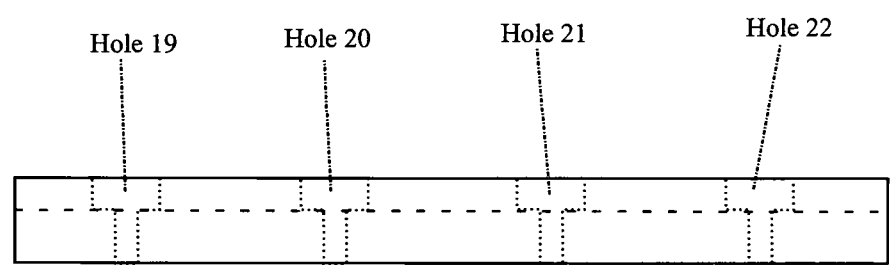

Fig. 8.1

Fig. 8.2
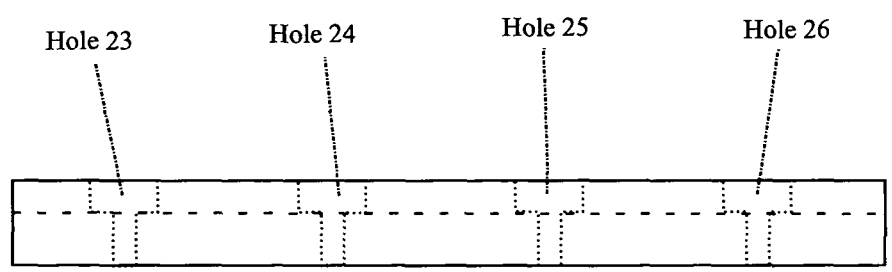

1 PHILLIPS DRIVE

LIGAMENT END-FEEL SIMULATOR

RELATED APPLICATIONS

This application claims the benefit of U.S. Provisional Application No. 62/231,589 filed on Jul. 10, 2015, entitled "Ligament End-Feel Simulator", which is incorporated herein by reference in its entirety.

BACKGROUND OF THE INVENTION

Field of Invention

The present invention relates to an orthopedic manual "special test" called the "Lachman Test". Whereas an examiner will use this "Lachman Test" on a patient to determine whether or not the anterior cruciate ligament (ACL) in the knee has been compromised. The present invention has the sole purpose of teaching Athletic Training students what said compromised (ACL) ligament resembles. This device simulates what a positive and negative "Lachman Test" would feel like to an examiner, thus determining an injured or non-injured ACL by the said ligament's "end feel". "End Feel" describes a ligament's "laxity" or looseness; this amount of "laxity" determines whether or not an examiner diagnoses a ligament as being compromised or not.

Description of the Prior Art

The "Lachman Test" is a manual "special test" used by Orthopedic Physicians and other medical professionals to determine the condition of the "Anterior Cruciate Ligament" (ACL). The test involves the examiner applying an anterior translation of the tibia (lower leg) upon the femur (thigh) at the knee joint.

One problem with teaching the "Lachman Test" is that most, if not all, Athletic Training (AT) students have to be taught and learn the special test technique on an uninjured patient.

Another problem with teaching Athletic Training (AT) students the "Lachman Test" is that many of the best Athletic Training programs are Division One universities and colleges. These universities and colleges give a lot of money in scholarships to their "student athletes".

A major problem with these Division One programs is, that because they give a large sum of money to these "student athletes", these "student athletes" become investments to their program.

A problem with these "student athletes" becoming an investment is that, these universities and colleges only want "professional physicians" and "Certified Athletic Trainers" to examine and diagnose the injuries of the said "student athletes".

Another problem is that the (AT) students never learn how to properly diagnose an injured patient's knee because they can never use the "Lachman Test" on an injured patient. Hence never feeling the difference between an injured and an uninjured ACL.

BRIEF SUMMARY OF THE INVENTION

Most of the "Knee Simulators" known to be in the art completely disregard the above problems, all of these and other problems are eliminated by the Ligament End-Feel Simulator of the present invention.

Most, if not all, of the knee simulators in the art are used for creating prosthetics for knee replacements or obtaining an exact measurement of laxity on an already injured patient.

An object of this invention is to allow an examiner to apply the "Lachman Test" to the device, with the result of the device simulating the anterior translation of the tibia on the femur that the "Lachman Test" causes on an actual human knee, when applied by an examiner.

Another object of this invention is to completely eliminate the need for a real life patient when teaching AT students this manual special test.

Another object of this invention is to provide AT students with a means of palpating an injured ACL compared to an uninjured ACL, without ever touching a real person. This capability is completely new to the art of Athletic Training.

BRIEF DESCRIPTION OF THE SEVERAL VIEWS OF THE DRAWING

FIG. 1.1 is an (ordinary) view from the front/side (of the [base 1]) of a [Ligament End Feel Simulator] made according to the present invention.

FIG. 2 is a (sectional) view from the front/side (of the [top handle $^2$]) of a [Ligament End Feel Simulator] (with screws removed to show holes for screw placement) made according to the present invention.

FIG. 2.1 is a (sectional) view from the side (of the [top handle 2]) of a [Ligament End Feel Simulator] made according to the present invention (shown in advantage).

FIG. 3.1 is a (sectional/ordinary) view from the front/side (of the [movement arm 3]) of a [Ligament End Feel Simulator] made according to the present invention (shown to advantage).

FIG. 4.1 is a (sectional) view from the front (of the [front hinge 4]) of a [Ligament End Feel Simulator] (with Hole 35 labeled) made according to the present invention (shown to advantage).

FIG. 4.2 is a (sectional) view from the front (of the [elevator hinge $^5$]) of a [Ligament End Feel Simulator] (with Hole 36 labeled) made according to the present invention (shown to advantage).

FIG. 4.3 is a (sectional) view from the front/side (of the [elevator hinge 5]) of a [Ligament End Feel Simulator] (with [movement arm 3] detached. Also the [elevator hinge 5] is seen detached from the [internal elevator $^6$]) made according to the present invention.

FIG. 5.1 is a (sectional) view from the side (of the [right side panel]) (of the [internal box 7]) of a [Ligament End Feel Simulator] (where the screws are removed to show holes and said holes labeled) made according to the present invention (shown to advantage).

FIG. 5.2 is a (sectional) view from the side (of the [left side panel]) (of the [internal box 7]) of a [Ligament End Feel Simulator] (where the screws are removed to show holes and said holes labeled) made according to the present invention (shown to advantage).

FIG. 5.3 is a (sectional) view from the rear (of the [rear panel]) (of the [internal box 7]) of a [Ligament End Feel Simulator] (where the screws are removed to show holes and said holes labeled) made according to the present invention (shown to advantage).

FIG. 6.1 is a (sectional/ordinary) view from the side (of the [right quadrilateral panel] of the [internal elevator 6]) of a [Ligament End Feel Simulator] (where the screws are removed to show holes and said holes labeled) made according to the present invention (shown to advantage).

FIG. 6.2 is a (sectional/ordinary) view from the side (of the [left quadrilateral panel] of the [internal elevator 6]) of a [Ligament End Feel Simulator] (where the screws are removed to show holes and said holes labeled) made according to the present invention (shown to advantage).

FIG. 6.3 is a (sectional/ordinary) view from above (of the [internal elevator 6]) of a [Ligament End Feel Simulator] (where the fluid filled sphere 13 has been removed to show holes and said holes labeled) made according to the present invention (shown to advantage).

FIG. 6.4 is a (sectional/ordinary) view from the front (of the [internal elevator 6]) of a [Ligament End Feel Simulator] made according to the present invention (shown to advantage).

FIG. 7.1 is a (ordinary) view from the front (of the [Rail 1 8]) of a [Ligament End Feel Simulator] (where screws and guides are missing to show cavities and holes with said holes being labeled) made according to the present invention (shown to advantage).

FIG. 7.2 is a (ordinary) view from the side (of the [Rail 1 8]) of a [Ligament End Feel Simulator] (where screws and guides are missing to show cavities and holes with said holes being labeled) made according to the present invention (shown to advantage).

FIG. 8.1 is a (ordinary) view from the front (of the [Rail 2 9]) of a [Ligament End Feel Simulator] (where screws and guides are missing to show cavities and holes with said holes being labeled) made according to the present invention (shown to advantage).

FIG. 8.2 is a (ordinary) view from the side (of the [Rail 2 9]) of a [Ligament End Feel Simulator] (where screws and guides are missing to show cavities and holes with said holes being labeled) made according to the present invention (shown to advantage).

FIG. 9.1 is a (ordinary) view from the front (of the [guide 1 10]) of a [Ligament End Feel Simulator] (where screws are missing to show cavities and holes with said holes being labeled) made according to the present invention.

FIG. 10.1 is a (ordinary) view from the front (of the [guide 2 11]) of a [Ligament End Feel Simulator] (where screws are missing to show cavities and holes with said holes being labeled) made according to the present invention.

FIG. 13.1 is an (ordinary) view from the side (of the [internal screw]) of a Ligament End Feel Simulator made according to the present invention (shown in advantage).

FIG. 14.1 is an (ordinary) view from the top (of the [handle screw]) of a Ligament End Feel Simulator made according to the present invention (shown in advantage).

DETAILED DESCRIPTION OF THE INVENTION

An embodiment to be preferred of the [Ligament End Feel Simulator] of the present invention is here and in figures disclosed. For clarity, within this document all reference to the front and rear of the [Ligament End Feel Simulator] will correspond to the [Ligament End Feel Simulator] as oriented in FIG. 1.1, the front of the figure when oriented such that the text is upright corresponding to the front of the [Ligament End Feel Simulator], and the rear of the figure when oriented such that the text is upright corresponding to the rear of the [Ligament End Feel Simulator]. Likewise, all reference to the left of the [Ligament End Feel Simulator] will correspond to the leftmost part of the [Ligament End Feel Simulator] as viewed in FIG. 1.1 when oriented with the text upright, and all reference to the right of the [Ligament End Feel Simulator] will correspond to the rightmost part of the [Ligament End Feel Simulator] as viewed in FIG. 1.1 when oriented with the text upright.

Figure 1:
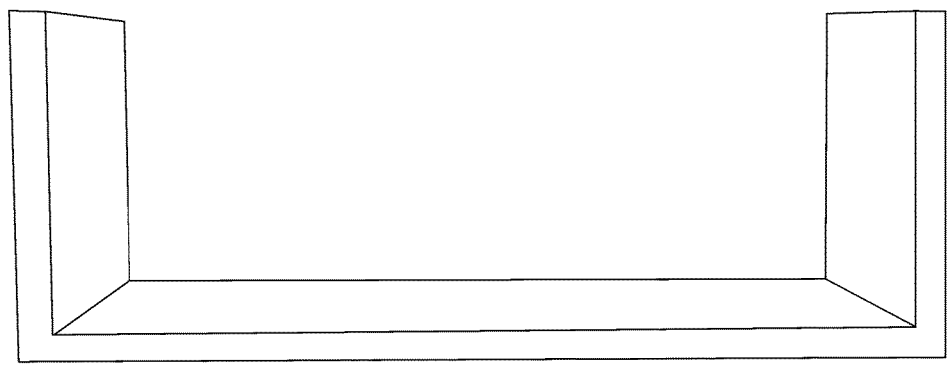
FIG. 1 is an (ordinary) view from the side (of the [base $^1$]) of a [Ligament End Feel Simulator] made according to the present invention.
Figure 1:
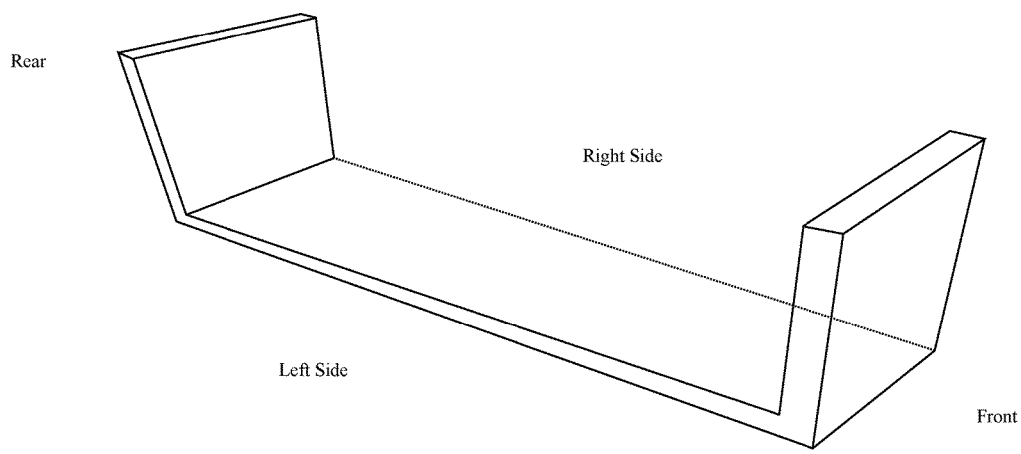
Figure 3:
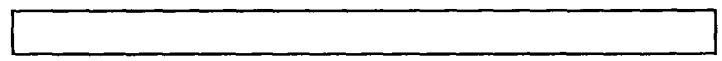
FIG. 3 is a (sectional) view from the side (of the [movement arm $^3$]) of a [Ligament End Feel Simulator] made according to the present invention (shown to advantage).
Figure 3:
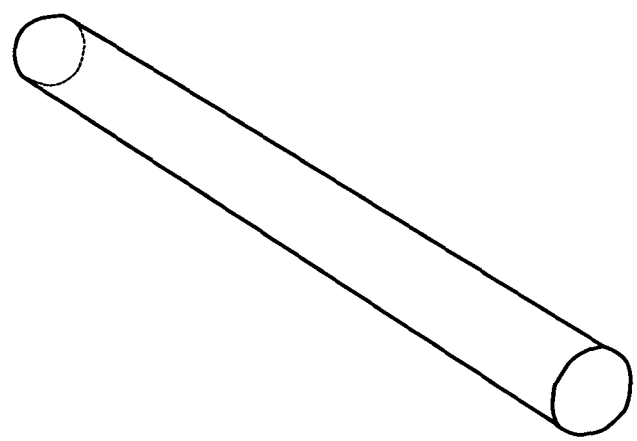
Figure 4:
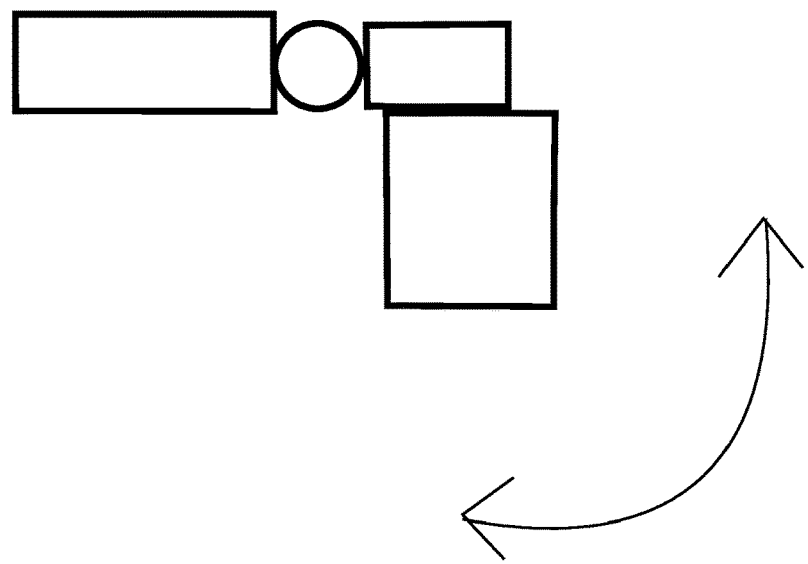
FIG. 4 is a (sectional) view from the side (of the [front hinge $^4$]) of a [Ligament End Feel Simulator] (with [movement arm 3] detached, as well as showing the direction of motion that the hinge allows) made according to the present invention.
Figure 4:
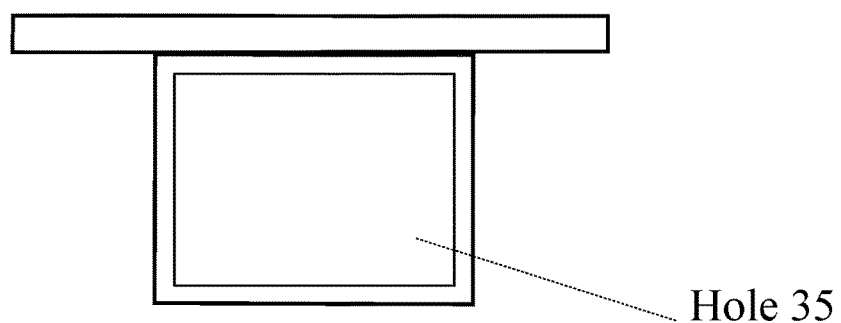

Referring to the figures, the [Ligament End Feel Simulator] of the present invention comprises generally of: FIGS. 1 and 1.1 which are views of the base 1 of the device which is stationary with no moving parts, but is the frame for other parts to attach to. FIGS. 2 and 2.1 show views of the top handle 2 which attaches to the base 1 at the rear of the top handle 2 and the front of the top handle 2 attaches to the rear of the internal box 7. FIGS. 3 and 3.1 show views of the movement arm 3 which articulates with the front hinge 4 to allow an up and down motion of the movement arm 3. The movement arm 3 also articulates with the elevator hinge 5, when the said up and down motion occurs, it causes the internal elevator 6 to also translate up and down. FIG. 4, 4.1 shows the front hinge 4 which attaches to the front inner side of the base 1. FIG. 4.1 also shows hole 35 where the movement arm 3 will insert into the front hinge 4. FIGS. 4.2 and 4.3 show the elevator hinge 5 which attaches to the front of the internal elevator 6. FIGS. 4.2 and 4.3 also show hole 36 where the rear of the movement arm 3 inserts into the elevator hinge 5 to allow the up and down translation of the internal elevator 6 when said translation occurs on the movement arm 3.

Figure 5:
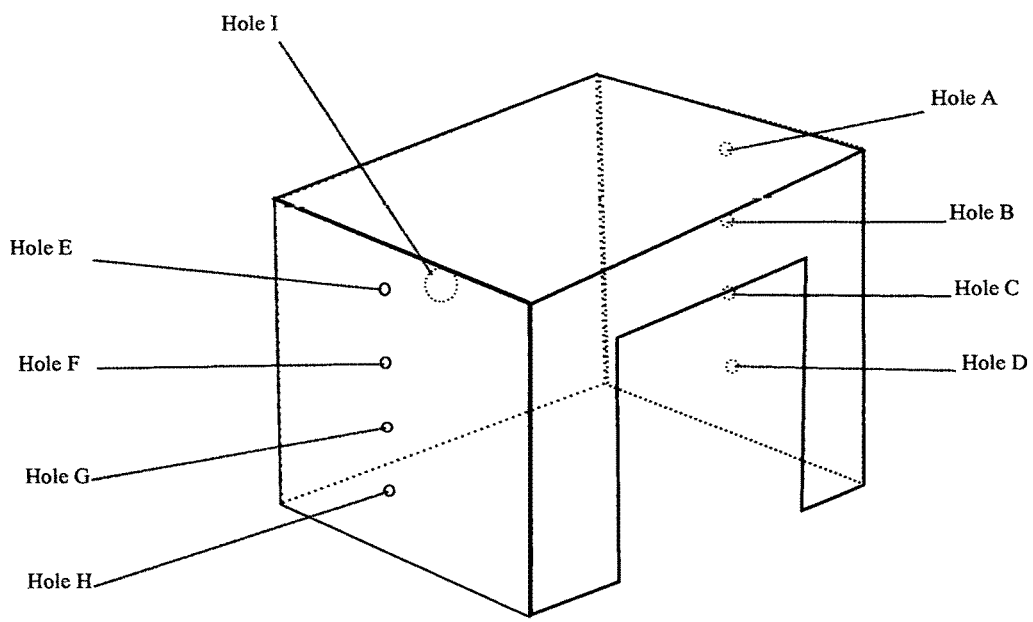
FIG. 5 is a (ordinary/sectional) view from the front/side (of the [internal box $^7$]) of a [Ligament End Feel Simulator] (with screws removed to show holes, and those holes labeled) made according to the present invention (shown to advantage).

Referring to the figures, the [Ligament End Feel Simulator] of the present invention comprises generally of: FIG. 5 which is the internal box 7 where the rear of the internal box 7 attaches to the front of the top handle 2 by screw 5 which is inserted into hole I at the rear of the internal box. FIG. 5.1 shows the right panel of the internal box 7 with holes A, B, C and D labeled. FIG. 5.2 shows the left panel of the internal box 7 with holes E, F, G, and H labeled. FIG. 5.3 shows the rear panel of the internal box 7 with hole I labeled.

Figure 6:
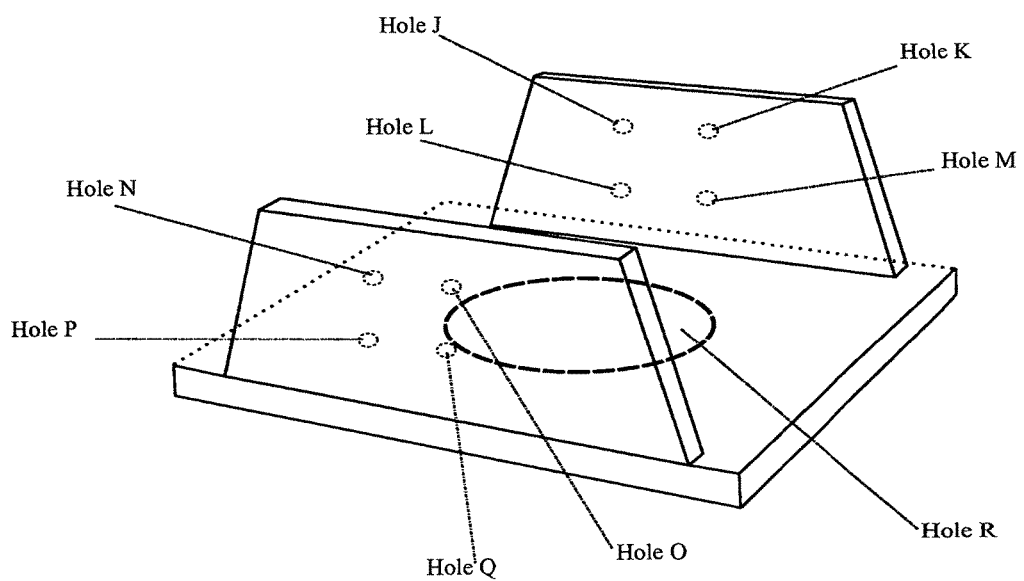
FIG. 6 is a (sectional/ordinary) view from the front/side (of the [internal elevator 6]) of a [Ligament End Feel Simulator] (where the screws and fluid filled sphere 13 are removed to show holes and said holes labeled) made according to the present invention (shown to advantage).

Referring to the figures, the [Ligament End Feel Simulator] of the present invention comprises generally of: FIG. 6 which shows the internal elevator 6 with all pieces attached accept the elevator hinge 5. FIG. 6.1 shows the right piece of the internal elevator 6 with holes J, K, L and M labeled. FIG. 6.2 shows the left piece of the internal elevator with holes N, O, P, and Q labeled. FIG. 6.3 shows the bottom piece of the internal elevator with hole R labeled. FIG. 6.4 shows the internal elevator 6 with the elevator hinge 5 attached and hole 35 labeled.

Figure 7:
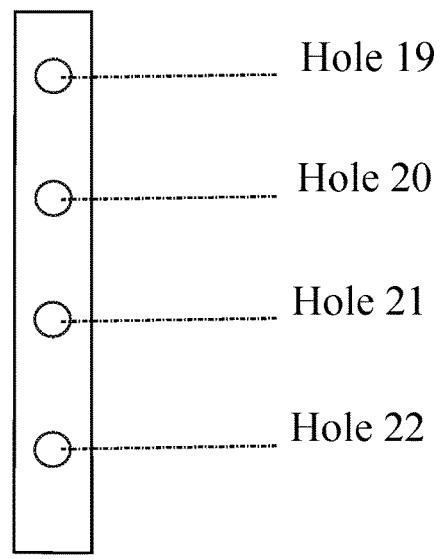
FIG. 7 is a (ordinary) view from above (of the [Rail 1 $^8$]) of a [Ligament End Feel Simulator] (where screws and guides are missing to show cavities and holes with said holes being labeled) made according to the present invention (shown to advantage).
Figure 7:
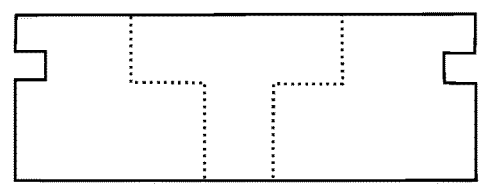

Referring to the figures, the [Ligament End Feel Simulator] of the present invention comprises generally of: FIG. 7 which shows Rail 1 8, which is to be attached to the right side panel of the internal box 7 by screw 1 which passes through hole 20 of rail 1 8 and hole B of the right side panel of the internal box 7, and screw 2 which passes through hole 22 of rail 1 8 and hole D of the right side panel of the internal box 7. Also holes 19, 20, 21, and 22 are labeled on rail 1 8. FIG. 7.1 shows the front of rail 1 8 where bilateral grooves can been seen where guide 1 10 will insert into rail 1 8 allowing guide 1 10 to slide back and forth on rail 1 8. FIG. 7.2 shows rail 1 8 and holes 19, 20, 21, and 22 labeled. This configuration is used to simulate a non-injured ACL.

Figure 8:
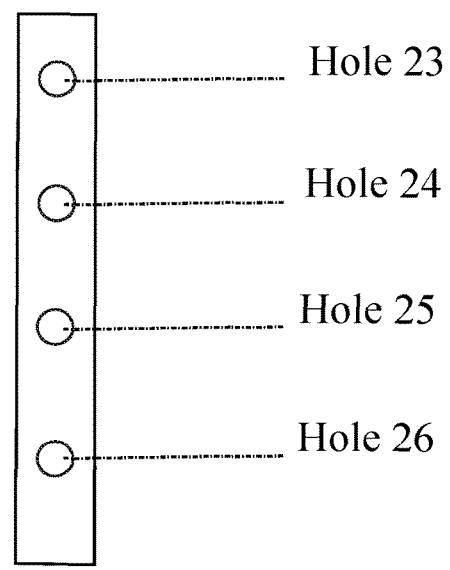
FIG. 8 is a (ordinary) view from above (of the [Rail 2 $^9$]) of a [Ligament End Feel Simulator] (where screws and guides are missing to show cavities and holes with said holes being labeled) made according to the present invention (shown to advantage).
Figure 8:
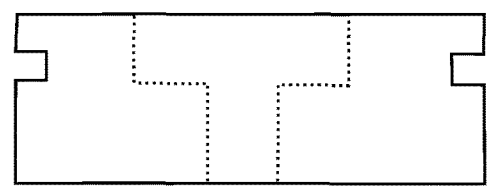

Referring to the figures, the [Ligament End Feel Simulator] of the present invention comprises generally of: FIG. 8 which shows Rail 2 9, which is to be attached to the left side panel of the internal box 7 by screw 3 which passes through hole 24 of rail 2 9 and hole F of the left side panel of the internal box 7, and screw 4 which passes through hole 26 of rail 2 9 and hole H of the left side panel of the internal box 7. Also holes 23, 24, 25, and 26 are labeled on rail 2 9. FIG. 8.1 shows the front of rail 2 9 where bilateral grooves can been seen where guide 2 11 will insert into rail 2 9 allowing guide 2 11 to slide back and forth on rail 2 9. FIG. 8.2 shows rail 2 9 and holes 23, 24, 25, and 26 labeled. This configuration is used to simulate a non-injured ACL.

Referring to the figures, the [Ligament End Feel Simulator] of the present invention comprises generally of: FIG. 7 which shows Rail 1 8, which is to be attached to the right side panel of the internal box 7 by screw 1 which passes through hole 19 of rail 1 8 and hole A of the right side panel of the internal box 7, and screw 2 which passes through hole 22 of rail 1 8 and hole D of the right side panel of the internal box 7. Also holes 19, 20, 21, and 22 are labeled on rail 1 8. FIG. 7.1 shows the front of rail 1 8 (8) where bilateral grooves can been seen where guide 1 10 will insert into rail 1 8 allowing guide 1 10 to slide back and forth on rail 1 8. FIG. 7.2 shows rail 1 8 and holes 19, 20, 21, and 22 labeled. This configuration is used to simulate an injured ACL.

Referring to the figures, the [Ligament End Feel Simulator] of the present invention comprises generally of: FIG. 8 which shows Rail 2 9, which is to be attached to the left side panel of the internal box 7 by screw 3 which passes through hole 23 of rail 2 9 and hole E of the left side panel of the internal box 7, and screw 4 which passes through hole 26 of rail 2 9 and hole H of the left side panel of the internal box 7. Also holes 23, 24, 25, and 26 are labeled on rail 2 9. FIG. 8.1 shows the front of rail 2 9 where bilateral grooves can been seen where guide 2 11 will insert into rail 2 9 allowing guide 2 11 to slide back and forth on rail 2 9. FIG. 8.2 shows rail 2 9 and holes 23, 24, 25, and 26 labeled. This configuration is used to simulate an injured ACL.

Figure 9:
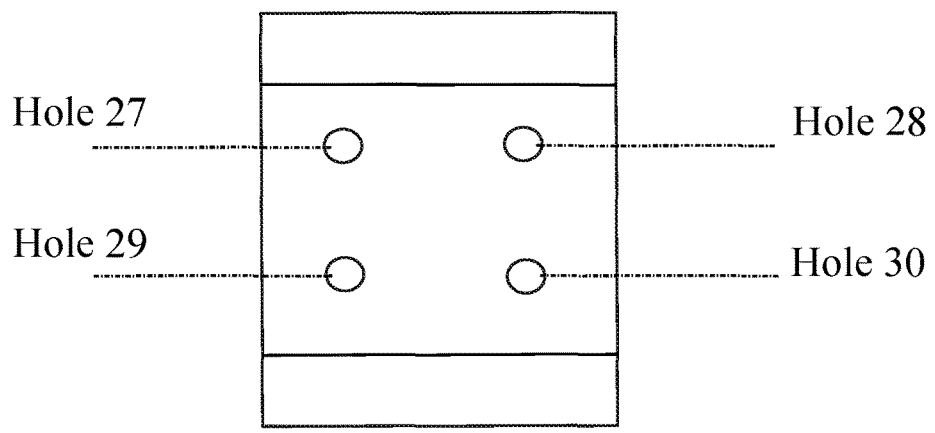
FIG. 9 is a (ordinary) view from above (of the [guide 1 $^{10}$]) of a [Ligament End Feel Simulator] (where screws are missing to show cavities and holes with said holes being labeled) made according to the present invention.
Figure 9:
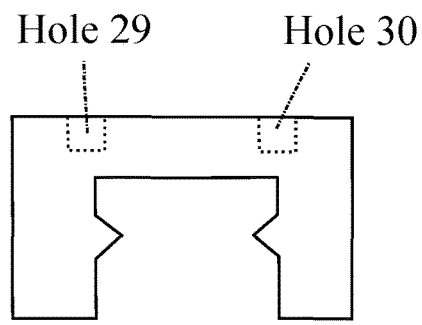

Referring to the figures, the [Ligament End Feel Simulator] of the present invention comprises generally of: FIG. 9 shows guide 1 10, with holes 27, 28, 29, and 30 labeled. Guide 1 10 is to be attached to the right side piece of the internal elevator 6 by screw 6 which inserts into hole J of the right side piece of the internal elevator 6 and screws into hole 27 of guide 1 10. Guide 1 10 is also to be attached to the right side piece of the internal elevator 6 by screw 7 which inserts into hole K of the right side piece of the internal elevator 6 and screws into hole 28 of guide 1 10. Guide 1 10 also to be attached to the right side piece of the internal elevator 6 by screw 8 which inserts into hole L of the right side piece of the internal elevator 6 and screws into hole 29 of guide 1 10. Guide 1 10 is to be attached to the right side piece of the internal elevator 6 by screw 9 which inserts into hole M of the right side piece of the internal elevator 6 and screws into hole 30 of guide 1 10. FIG. 9.1 shows the bilateral tracks of guide 1 10 where guide 1 10 will move along the grooves of rail 1 8.

Figure 10:
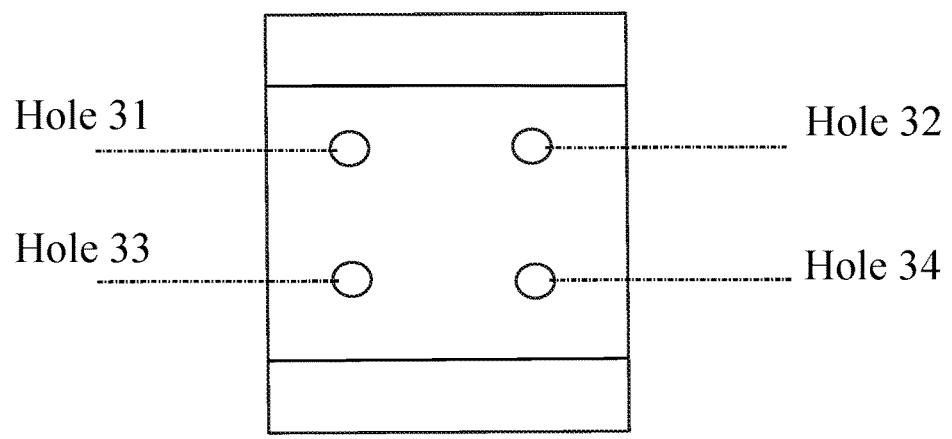
FIG. 10 is a (ordinary) view from above (of the [guide 2 $^{11}$]) of a [Ligament End Feel Simulator] (where screws are missing to show cavities and holes with said holes being labeled) made according to the present invention.
Figure 10:
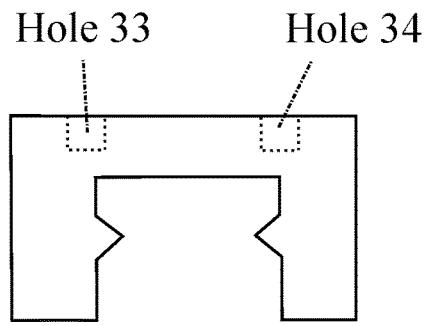

Referring to the figures, the [Ligament End Feel Simulator] of the present invention comprises generally of: FIG. 10 shows guide 2 11, with holes 31, 32, 33, and 34 labeled. Guide 2 11 is to be attached to the left side piece of the internal elevator 6 by screw 10 which inserts into hole N of the left side piece of the internal elevator 6 and screws into hole 31 of guide 2 11. Guide 2 11 is also to be attached to the left side piece of the internal elevator 6 by screw 11 which inserts into hole O of the left side piece of the internal elevator 6 and screws into hole 32 of guide 2 11. Guide 2 11 also to be attached to the left side piece of the internal elevator 6 by screw 12 which inserts into hole P of the left side piece of the internal elevator 6 and screws into hole 33 of guide 2 11. Guide 2 11 is to be attached to the left side piece of the internal elevator 6 by screw 13 which inserts into hole Q of the left side piece of the internal elevator 6 and screws into hole 34 of guide 2 11. FIG. 10.1 shows the bilateral tracks of guide 2 11 where guide 2 11 will move along the grooves of rail 2 9.

Figure 11:
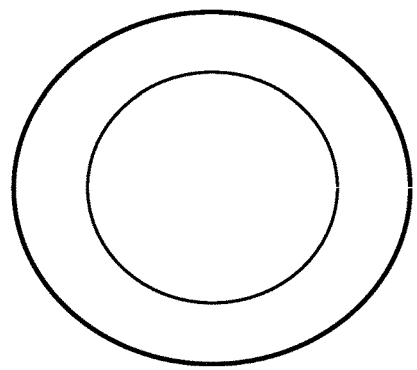
FIG. 11 is a (sectional/ordinary) view from the front (of the [external rubber washer $^{12}$]) of a [Ligament End Feel Simulator] (where screws are missing to show cavities and holes with said holes being labeled) made according to the present invention (shown in advantage).

Referring to the figures, the [Ligament End Feel Simulator] of the present invention comprises generally of: FIG. 11 shows the external rubber washer 12 which is to placed between the front of the top handle 2 and the rear of the internal box 7.

Figure 12:
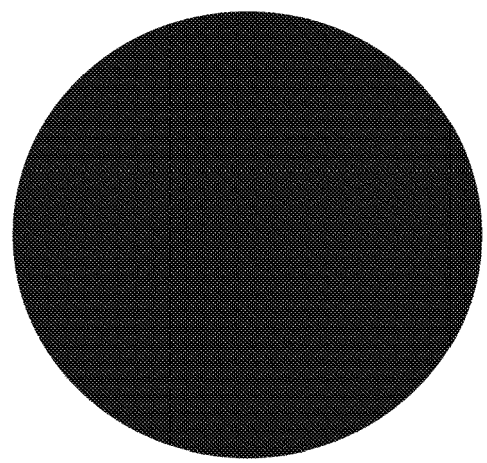
FIG. 12 is a (ordinary) view from the front/side (of the [fluid filled sphere $^{13}$]) of a [Ligament End Feel Simulator] made according to the present invention.

Referring to the figures, the [Ligament End Feel Simulator] of the present invention comprises generally of: FIG. 12 which shows the fluid filled sphere 13 which sits in hole R of the internal elevator 6 and is enclosed inside the internal box 7.

Figure 13:
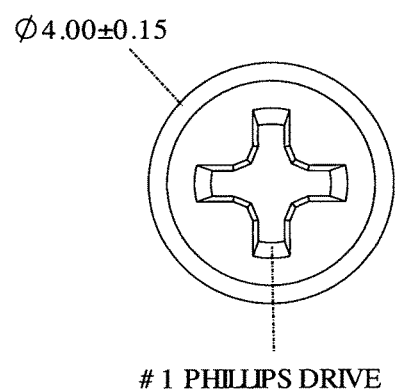
FIG. 13 is an (ordinary) view from the top (of the [internal screw]) of a Ligament End Feel Simulator made according to the present invention (shown in advantage).
Figure 13:
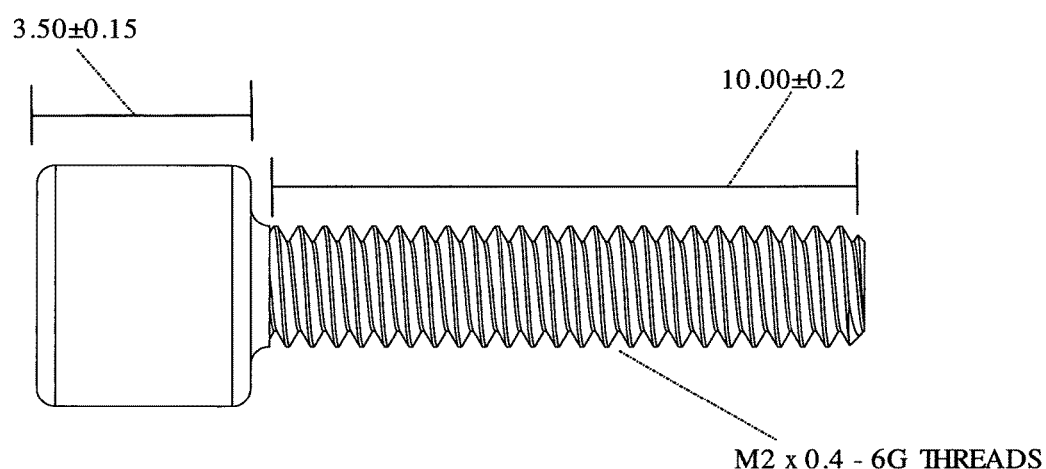

Referring to the figures, the [Ligament End Feel Simulator] of the present invention comprises generally of: FIG. 13 and FIG. 13.1 which shows the specifications of the internal screws.

Figure 14:
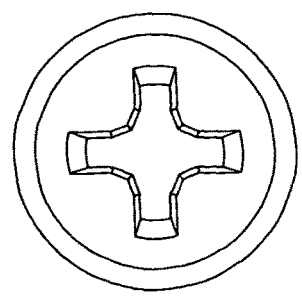
FIG. 14 is an (ordinary) view from the side (of the [handle screw]) of a Ligament End Feel Simulator made according to the present invention (shown in advantage).
Figure 14:
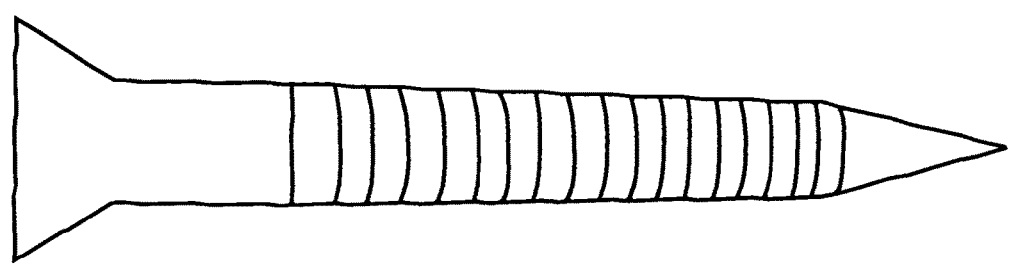

Referring to the figures, the [Ligament End Feel Simulator] of the present invention comprises generally of: FIGS. 14 and 14.1 which shows the specifications of the handle screw.

Figure 15:
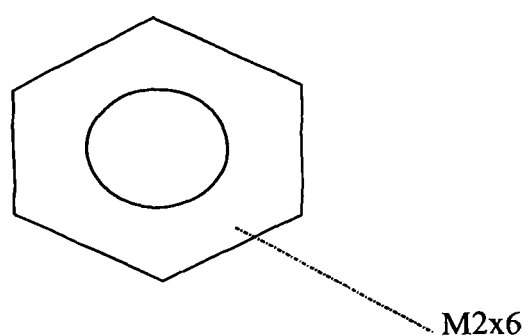
FIG. 15 is an (ordinary) view from the front (of the [nut]) of a Ligament End Feel Simulator made according to the present invention (shown in advantage).

Referring to the figures, the [Ligament End Feel Simulator] of the present invention comprises generally of: FIG. 15 which shows the [Ligament End Feel Simulator] shows the specifications of the nuts that will fasten to the ends of all internal screws.

Figure 16:
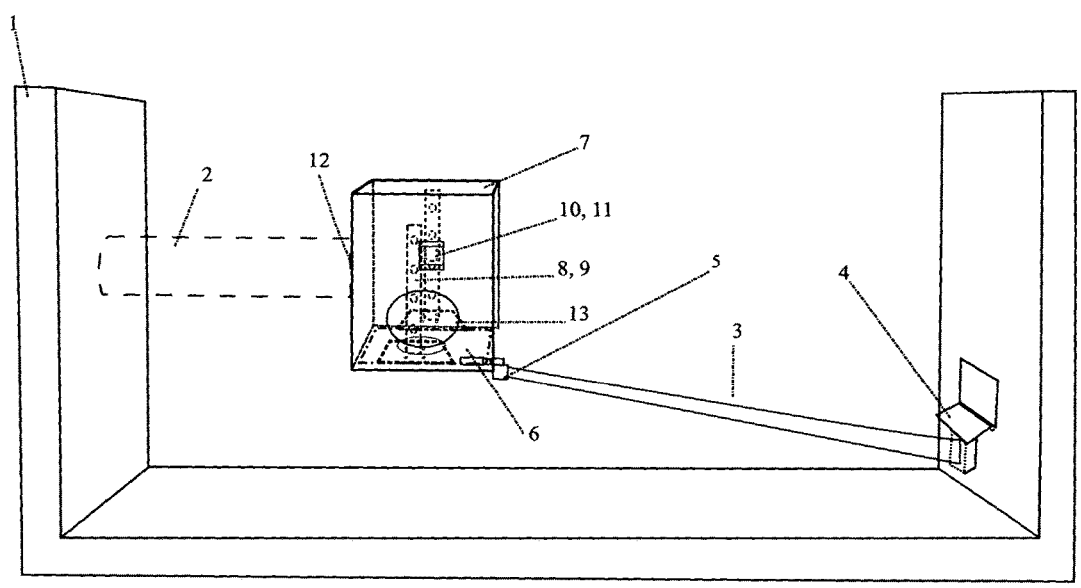
FIG. 16 is an (ordinary) view from the front/side of a Ligament End Feel Simulator (where all parts are numbered) made according to the present invention (fully assembled).

Referring to the figures, the [Ligament End Feel Simulator] of the present invention comprises generally of: FIG. 16 which shows the [Ligament End Feel Simulator] completely assembled.

Referring to functionality of the [Ligament End Feel Simulator]: The device is designed to simulate the "end feel" or "laxity" of the anterior cruciate ligament (ACL) of the knee. The degree of "end feel" or "laxity" determines whether or not the ACL has been injured or compromised. In order to obtain this degree of "end feel" or "laxity", an examiner must apply the "Lachman test". The "Lachman test" involves the examiner placing their stationary hand on the patient's lower thigh, above the patella, and their translating hand on the patient's upper lower leg under the patella. The examiner will then proceed to manually cause an anterior translation of the tibia upon the femur. In clearer terms: with the examiner's "stationary hand" not moving, the "translating" hand will pull the patient's lower leg "up" or "anteriorly" towards the examiner. This technique causes a manual anterior translation of the tibia (lower leg) on the femur (upper leg). The "ACL" is designed to specifically prevent this type of anterior translation of the tibia on the femur. The degree of translation ("end feel" or "laxity") that is felt by the examiner will determine if the "ACL" is compromised or not. A firm "end feel" will determine a non-injured "ACL", where a loose or greater "end feel" will determine an injured "ACL".

Referring to functionality of the [Ligament End Feel Simulator]: The [Ligament End Feel Simulator] mimics these very same motions and conditions. The examiner's "stationary" hand will be placed on the [top handle 2] of the [Ligament End Feel Simulator] and the examiner's "translating" hand will be place on the [movement arm 3] of the [Ligament End Feel Simulator]. When the examiner applies the "Lachman test", the device will simulate the anterior translation that would occur in a real life patient. The [top handle 2] will replace the lower thigh (femur) and the [movement arm 3] will replace the upper lower leg (tibia). The knee joint itself is comprised of the [internal box 7], [internal elevator 6], [rail 1 and 2], [guides 1 and 2], and [the fluid filled sphere 13]; when all are combined they simulate the "anterior translation" of the tibia on the femur.

Referring to functionality of the [Ligament End Feel Simulator]: The [front hinge 4] and [elevator hinge 5] connect the [movement arm 3] to the [internal elevator 6] and the front of the [base 1]. In "FIG. 4.2", hole 36 represents where the rear of the [movement arm 3] will insert into the [internal elevator 6]. In "FIG. 4.1", hole 35 represents where the front of the [movement arm 3] will insert into the [front hinge 4] which will be attached to the front of the [base 1]. Because the [internal elevator 6] and the [movement arm 3] are now connected, when the [movement arm 3] is raised or lowered the [internal elevator 6] will do the same. The raising of the [movement arm 3] and [internal elevator 6] in unison is what simulates the "anterior translation" of the upper lower leg (tibia) on the lower thigh (femur). The movement of the [internal elevator 6] inside of the [internal box 7] is facilitated by the [guides 1 and 2] which slide up and down along [rails 1 and 2]. The function of the [fluid filled sphere 13] is to simulate synovial fluid which is naturally present in a human knee.

It is to be appreciated that there are numerous materials such as wood, metal, or other plastics that may freely be altered or substituted to design or create the [base 1] of the [Ligament End Feel Simulator] of the present invention without altering the inventive concepts and principles embodied there in.

It is to be appreciated that there are numerous materials such as wood, metal, or other plastics that may freely be altered or substituted to design or create the [top handle 2] of the [Ligament End Feel Simulator] of the present invention without altering the inventive concepts and principles embodied there in.

It is to be appreciated that there are numerous materials such as wood, metal, or other plastics that may freely be altered or substituted to design or create the [internal box 7] of the [Ligament End Feel Simulator] of the present invention without altering the inventive concepts and principles embodied there in.

It is to be appreciated that there are numerous materials such as wood, metal, or other plastics that may freely be altered or substituted to design or create the [internal elevator 6] of the [Ligament End Feel Simulator] of the present invention without altering the inventive concepts and principles embodied there in.

It is to be appreciated that there are numerous materials such as wood, metal, or other plastics that may freely be altered or substituted to design or create the [internal box 7] of the [Ligament End Feel Simulator] of the present invention without altering the inventive concepts and principles embodied there in.

It is to be appreciated that there are numerous materials such as wood, metal, or other plastics that may freely be altered or substituted to design or create the [front hinge 4] of the [Ligament End Feel Simulator] of the present invention without altering the inventive concepts and principles embodied there in.

It is to be appreciated that there are numerous materials such as wood, metal, or other plastics that may freely be altered or substituted to design or create the [elevator hinge 5] of the [Ligament End Feel Simulator] of the present invention without altering the inventive concepts and principles embodied there in.

It is to be appreciated that there are numerous materials such as wood, metal, or other plastics that may freely be altered or substituted to design or create the [movement arm 3] of the [Ligament End Feel Simulator] of the present invention without altering the inventive concepts and principles embodied there in.

It is to be appreciated that there are numerous materials such as wood, metal, or other plastics that may freely be altered or substituted to design or create the [rail 1 8] of the [Ligament End Feel Simulator] of the present invention without altering the inventive concepts and principles embodied there in.

It is to be appreciated that there are numerous materials such as wood, metal, or other plastics that may freely be altered or substituted to design or create the [rail 2 9] of the

[Ligament End Feel Simulator] of the present invention without altering the inventive concepts and principles embodied there in.

It is to be appreciated that there are numerous materials such as wood, metal, or other plastics that may freely be altered or substituted to design or create the [guide 1 10] of the [Ligament End Feel Simulator] of the present invention without altering the inventive concepts and principles embodied there in.

It is to be appreciated that there are numerous materials such as wood, metal, or other plastics that may freely be altered or substituted to design or create the [guide 2 11] of the [Ligament End Feel Simulator] of the present invention without altering the inventive concepts and principles embodied there in.

It is to be appreciated that there are numerous materials such as wood, other plastics and even different types of metals such as aluminum, zinc, copper that may freely be altered or substituted to design or create the [internal screws] of the [Ligament End Feel Simulator] of the present invention without altering the inventive concepts and principles embodied there in.

It is to be appreciated that any device or apparatus which is designed to simulate "end feel" or "laxity" of the anterior cruciate ligament (ACL) of the knee when the "lachman test", "the anterior drawer test", or any other versions of a manual test where there is a simulated "anterior translation" of the tibia on the femur by an examiner with the purpose of teaching a student, pupil, athletic training student, certified athletic trainer, medical student, medical doctor, emergency medical technician, paramedic, nurse, orthopedic assistant, first responder or any other medical professional without the presence of an actual real life patient may be designed of the present invention without altering the inventive concepts and principles embodied there in.

CLOSING STATEMENT

Having thus described in detail a preferred embodiment of the [Ligament End Feel Simulator] of the present invention, it is to be appreciated and will be apparent to those skilled in the art that many changes not exemplified in the detailed description of the invention could be made without altering the inventive concepts and principles embodied therein. It is also to be appreciated that numerous embodiments only incorporating only part of the preferred embodiment are possible that do not alter, with respect to those parts, the inventive concepts and principles embodied therein. The presented embodiments are therefore to be considered in all respects exemplary and/or illustrative and not restrictive, the scope of the invention being indicated by the appended claims, and all alternate embodiments and changes to the embodiments shown herein that come within the meaning and range of equivalency of the appended claims are therefore to be embraced therein.

[1] Base
[2] Top Handle
[3] Movement Arm
[4] Front Hinge
[5] Elevator Hinge
[6] Internal Elevator
[7] Internal Box
[8] Rail 1
[9] Rail 2
[10] Guide 1
[11] Guide 2
[12] External Rubber Washer
[13] Fluid Filled Sphere

I claim:

1. A Ligament End Feel Simulator for teaching injury evaluation techniques for the anterior cruciate ligament including the Lachman special test, comprising in combination:

A simulated human form including the knee, said knee containing a base, stationary arm, internal box, internal elevator, and movement arm, said stationary arm is mounted to the internal box and base of the device by two separate screws, one which inserts at the rear of the stationary arm which mounts the stationary arm to the base, and the other which inserts at the rear of the internal box and fastens into the front of the stationary arm, said internal elevator is fastened to the internal box by a pair of rails and guides, said internal elevator is fastened to the movement arm by a hinge mounted to the bottom of the internal elevator, said movement arm is mounted to the base by a separate hinge located at the front of the base.

2. The ligament end feel simulator according to claim 1 where said knee is a cross section of an human knee and has lengthwise dimensions.

3. The ligament end feel simulator according to claim 1 where said stationary arm simulates the femur of an adult, where said stationary arm and internal box simulate the patellar femoral joint of the human knee, where said internal elevator and movement arm simulates the tibia and tibiofemoral joint of the human knee.

4. The ligament end feel simulator according to claim 3 where said internal elevator is mounted within the internal box, said guides and rails which allow the raising and lowering of the internal elevator within the internal box simulating the anterior translation of the tibia on the femur.

5. The ligament end feel simulator according to claim 4 where said rails and guides are fastened to the inner portion of the internal box.

6. The ligament end feel simulator according to claim 1 where said simulator mimics, duplicates, replicates, or imitates the anterior translation of the tibia on the femur with the intent of providing educational information on the degree of laxity of the anterior cruciate ligament.

* * * * *